United States Patent
Helson et al.

(10) Patent No.: US 11,806,401 B2
(45) Date of Patent: *Nov. 7, 2023

(54) PREVENTION OF DRUG-INDUCED ATRIO-VENTRICULAR BLOCK

(71) Applicant: SignPath Pharma Inc., Sandy, UT (US)

(72) Inventors: Lawrence Helson, Quakertown, PA (US); Annie Bouchard, Stoke (CA)

(73) Assignee: Signpath Pharma, Inc., Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/494,932

(22) Filed: Apr. 24, 2017

(65) Prior Publication Data

US 2017/0312366 A1 Nov. 2, 2017

Related U.S. Application Data

(60) Provisional application No. 62/328,307, filed on Apr. 27, 2016.

(51) Int. Cl.

| | | |
|---|---|---|
| *A61K 9/127* | (2006.01) | |
| *A61K 47/24* | (2006.01) | |
| *A61K 31/685* | (2006.01) | |
| *A61K 9/00* | (2006.01) | |
| *A61K 31/137* | (2006.01) | |
| *A61K 31/277* | (2006.01) | |
| *A61K 31/4709* | (2006.01) | |
| *A61K 49/00* | (2006.01) | |

(52) U.S. Cl.
CPC ............ *A61K 47/24* (2013.01); *A61K 9/0053* (2013.01); *A61K 9/127* (2013.01); *A61K 31/137* (2013.01); *A61K 31/277* (2013.01); *A61K 31/4709* (2013.01); *A61K 31/685* (2013.01); *A61K 49/0008* (2013.01)

(58) Field of Classification Search
None
See application file for complete search history.

(56) References Cited

U.S. PATENT DOCUMENTS

| | | |
|---|---|---|
| 4,812,312 A | 3/1989 | Lopez-Berestein et al. |
| 5,023,087 A | 6/1991 | Yao-Young |
| 5,679,864 A | 10/1997 | Krackov et al. |
| 6,143,276 A | 11/2000 | Unger |
| 6,143,321 A | 11/2000 | Needham |
| 6,787,132 B1 | 9/2004 | Gabison et al. |
| 6,946,475 B1 | 9/2005 | Lloyd |
| 7,060,733 B2 | 6/2006 | Pandol et al. |
| 7,507,864 B2 | 3/2009 | Miller et al. |
| 7,674,820 B2 | 3/2010 | Fedida et al. |
| 7,723,515 B1 | 5/2010 | Dimauro |
| 7,871,609 B2 | 1/2011 | Ziff et al. |
| 7,968,115 B2 | 6/2011 | Kurzrock et al. |
| 8,062,663 B2 | 11/2011 | Wang et al. |
| 8,133,897 B2 | 3/2012 | Ritzen et al. |
| 8,153,172 B2 | 4/2012 | Antony |
| 8,202,839 B1 | 6/2012 | Sung |
| 8,207,219 B2 | 6/2012 | Fedida et al. |
| 8,747,890 B2 | 6/2014 | Helson |
| 8,753,674 B2 | 6/2014 | Helson |
| 9,138,411 B2 | 9/2015 | Ranjan et al. |
| 9,682,041 B2 | 6/2017 | Helson |
| 10,117,881 B2 | 11/2018 | Helson |
| 10,238,602 B2 | 3/2019 | Helson |
| 10,258,691 B2 | 4/2019 | Ielson |
| 10,349,884 B2 | 7/2019 | Helson |
| 10,357,458 B2 | 7/2019 | Helson |
| 2001/0051184 A1 | 12/2001 | Heng |
| 2002/0048598 A1 | 4/2002 | Malik |
| 2002/0110586 A1 | 8/2002 | Madden |
| 2003/0129224 A1 | 7/2003 | Tardi et al. |
| 2005/0101674 A1 | 5/2005 | Maurer et al. |
| 2005/0181036 A1 | 8/2005 | Aggarwal et al. |
| 2005/0233970 A1 | 10/2005 | Garnick |
| 2005/0266067 A1 | 12/2005 | Sengupta et al. |
| 2006/0067998 A1 | 3/2006 | Kurzrock et al. |
| 2006/0147512 A1 | 7/2006 | Sabin |
| 2006/0269595 A1 | 11/2006 | Madden |
| 2007/0048284 A1 | 3/2007 | Donahue et al. |
| 2008/0075671 A1 | 3/2008 | Di Mauro |
| 2008/0103213 A1 | 5/2008 | Kurzrock et al. |

(Continued)

FOREIGN PATENT DOCUMENTS

| | | |
|---|---|---|
| CA | 2584279 A1 | 4/2005 |
| CN | 104758255 | 7/2015 |

(Continued)

OTHER PUBLICATIONS

Wikipedia (https://en.wikipedia.org/wiki/Lysophosphatidylcholine (downloaded Mar. 22, 2018).*
Yagi et al. (Analysis of Onset Mechanisms of a Sphingosine 1-Phosphate Receptor Modulator Fingolimod-Induced Atrioventricular Conduction Block and QT-Interval Prolongation. Toxicol Appl Pharmacol. Nov. 15, 2014;281(1):39-47).*
Zeltser et al (Drug-Induced Atrioventricular Block: Prognosis After Discontinuation of the Culprit Drug. Journal of the American College of Cardiology. vol. 44, Issue 1, Jul. 7, 2004, pp. 105-108).*
Wkipedia2 (https://en.wikipedia.org/wiki/Atrioventricular_block (downloaded on Jul. 26, 2018).*
Dhandapani, K. M., et al., "Curcumin suppresses growth and chemoresistance of human glioblastoma cells via AP-1 and NFκB transcription factors," J. Neurochem (2007) 102:522-538.

(Continued)

*Primary Examiner* — Jake M Vu
(74) *Attorney, Agent, or Firm* — Edwin S. Flores; Daniel J. Chalker; Chalker Flores, LLP (57) ABSTRACT

The present invention includes a method of treating a drug-induced atrioventricular (AV) block comprising: providing a subject in need of therapy a drug that is contraindicated to treat a disease or condition in the subject, wherein the drug causes an AV block, with an amount of a lipid sufficient to reduce or eliminate the AV block caused by the drug.

5 Claims, 2 Drawing Sheets

(56) References Cited

U.S. PATENT DOCUMENTS

| | | |
|---|---|---|
| 2008/0253961 A1 | 10/2008 | Braden et al. |
| 2008/0255464 A1 | 10/2008 | Vincent |
| 2009/0123530 A1 | 5/2009 | Betageri et al. |
| 2009/0143433 A1 | 6/2009 | Hendrix |
| 2009/0169610 A1 | 7/2009 | Yamazaki et al. |
| 2009/0181887 A1* | 7/2009 | Hansen .................. A61P 25/00 514/1.1 |
| 2009/0246770 A1 | 10/2009 | Levy |
| 2009/0291134 A1 | 11/2009 | Ateeq et al. |
| 2009/0317387 A1 | 12/2009 | Paton et al. |
| 2009/0324703 A1 | 12/2009 | Frautschy et al. |
| 2010/0004549 A1 | 1/2010 | Kohls et al. |
| 2010/0048957 A1 | 2/2010 | Kim |
| 2010/0068251 A1 | 3/2010 | Ali et al. |
| 2010/0093873 A1 | 4/2010 | Goldfischer |
| 2010/0120890 A1 | 5/2010 | Fedida |
| 2010/0151000 A1 | 6/2010 | Thomas et al. |
| 2010/0179103 A1 | 7/2010 | Desai |
| 2010/0239552 A1 | 9/2010 | Mayoux et al. |
| 2010/0240581 A1 | 9/2010 | Tortoriello et al. |
| 2010/0291043 A1 | 11/2010 | Medin et al. |
| 2011/0117186 A1 | 5/2011 | Helson |
| 2011/0200665 A1 | 8/2011 | Mei et al. |
| 2011/0229555 A1 | 9/2011 | Helson et al. |
| 2011/0287085 A1 | 11/2011 | Kurzrock et al. |
| 2012/0021036 A1 | 1/2012 | Majeti et al. |
| 2012/0031777 A1 | 2/2012 | Burke et al. |
| 2012/0040014 A1* | 2/2012 | Settineri ................ A23D 9/013 424/602 |
| 2012/0058208 A1 | 3/2012 | Jacob |
| 2012/0171280 A1 | 7/2012 | Zhang |
| 2012/0237590 A1 | 9/2012 | Helson |
| 2012/0308643 A1* | 12/2012 | Helson .................. A61K 9/127 424/450 |
| 2013/0310351 A1 | 11/2013 | Milan et al. |
| 2013/0337488 A1 | 12/2013 | Helson |
| 2014/0050780 A1 | 2/2014 | Cerundolo et al. |
| 2014/0065061 A1* | 3/2014 | Ranjan ................ A61K 9/1271 424/1.11 |
| 2015/0164878 A1 | 6/2015 | Helson |
| 2015/0343063 A1 | 12/2015 | Helson |
| 2016/0193149 A1 | 7/2016 | Helson |
| 2017/0035887 A1 | 2/2017 | Helson |
| 2017/0095489 A1 | 4/2017 | Helson |
| 2017/0119802 A1 | 5/2017 | Helson |
| 2017/0246110 A1 | 8/2017 | Helson |

FOREIGN PATENT DOCUMENTS

| | | |
|---|---|---|
| DE | 10029770 A1 | 12/2001 |
| EP | 3144006 | 9/2017 |
| JP | 10-2794887 | 10/1998 |
| JP | H10-191927 A | 7/2010 |
| JP | 2010275242 A | 12/2010 |
| JP | 2012-140395 | 7/2012 |
| WO | 2000070949 A1 | 11/2000 |
| WO | 2001093683 A1 | 12/2001 |
| WO | 2002002582 A1 | 1/2002 |
| WO | 2004047717 A2 | 6/2004 |
| WO | 2004080396 A2 | 9/2004 |
| WO | 2006061101 A2 | 6/2006 |
| WO | 2006131737 A2 | 12/2006 |
| WO | 2007062028 A2 | 5/2007 |
| WO | 2007103435 A2 | 9/2007 |
| WO | 2007129062 A1 | 11/2007 |
| WO | 2008045534 A2 | 4/2008 |
| WO | 2008063513 A2 | 5/2008 |
| WO | 2008093848 A1 | 7/2008 |
| WO | 2008128123 A1 | 10/2008 |
| WO | 2009051837 A2 | 4/2009 |
| WO | 2009073050 | 6/2009 |
| WO | 2010009186 A1 | 1/2010 |
| WO | 2010033692 A1 | 3/2010 |
| WO | 2010057332 A1 | 5/2010 |
| WO | 2011063178 A2 | 5/2011 |
| WO | 2011001351 A1 | 6/2011 |
| WO | 2011119588 A1 | 9/2011 |
| WO | 2012125830 A2 | 9/2012 |
| WO | 2012167212 A2 | 12/2012 |
| WO | 2013041894 | 3/2013 |
| WO | 2013166249 A1 | 11/2013 |
| WO | 2013188767 A1 | 12/2013 |
| WO | 2014036534 A1 | 3/2014 |
| WO | 2015095576 A1 | 6/2015 |

OTHER PUBLICATIONS

Extended European Search Report and European Search Opinion for 14864686.2 dated May 4, 2017, 8 pages.

Extended European Search Report and European Search Opinion for 16188460.6 dated Nov. 16, 2016, 12 pages.

Ramachandran, C., et al., "Potentiation of Etoposide and Temozolomide Cytotoxicity by Curcumin and Turmeric Force in Brain Tumer Cell Lines," Journal of Complementary and Integrative Medicine (2012), 9(1):Article 20.

International Search Report and Written Opinion for PCT/US2017/057446, dated Dec. 29, 2017, 13 pp.

Shopp, G.M., et al., "Liposomes ameliorate Crizotinib- and Nilotinib-induced inhibition of the cardiac IKr channel and Qtc prolongation," Anticancer Research, 2014, vol. 34, pp. 4733-4740.

Tang, H., et al., "Curcumin Polymers as Anticancer Conjugates," Biomaterials, vol. 31, No. 27, Jun. 29, 2010, pp. 7139-7149.

TASIGNA Package insert, Novartis Pharmaceuticals, Revised Sep. 2013.

Tonnesen, Hanne, H., et al., "Studies on curcumin and curcuminoids: XXV. Inhibition of primaquine-induced lysis of human red blood cells by curcumin," International Journal of Pharmaceutics 110, April 11, 1994 161-167.

Tudor, B-A, et al., "Amphotericin B@ treatment causes QT prolongation in lung transplant-pateints," Intensive Care Medicine Experimental, Oct. 2015, 3(Suppl 1):A213 poster presentation.

U.S. Department of Health and Human Services, "Guidance for Industry, S7B Nonclinical Evaluation of the Potential for Delayed Ventricular Repolarization (QT Interval Prolongation) by Human Pharmaceuticals," Oct. 2005, pp. 1-13.

Van De Water, et al., "An Improved Method to Correct the QT Interval of the Electrocardiogram for Changes in Heart Rate," Journal of Pharmacological Methods, Apr. 1989, vol. 22, pp. 207-217.

Van Dijck, P.W.M., et al., "Influence of Ca2+ and Mg2+ on the thermotropic behaviour and permeability properties of liposomes prepared from dimyristoyl phosphatidylglycerol and mixtures of dimyristoyl phosphatidylglycerol and dimyristoyl phosphatidylcholine," Biochimica et Biophysica Acta, Apr. 1975; 406:465-478.

Verma, Richa, et al., "Structural and functional changes in a syntheitic S5 segment of KvLQT1 channel as a result of a conserved amino acid substitution that occurs in LQT1 syndrome of human," Biochimica et Biophysica Acta, 1798, Jan. 2010, pp. 461-470.

Vidal, Alessandra Teixeira, et al., "Prolonged cardioprotective effect of pyridostigmine encapsulated in liposomes," Life Sciences, vol. 86, Oct. 20, 2009, pp. 17-23.

Vincenzi, Frank F., et al., "Citalopram-Induced Long QT Syndrome and the Mammalian Dive Reflex," Drug Saf—Case Rep, vol. 2:12, Aug. 1, 2015, 5 pp.

Wang, Jingxiong, et al., "Phospholipid metabolite 1-palmitoyl-lysophosphatidylcholine enhances human ether-a-go-go-related gene (HERG) K+ channel function", Circulation, Oct. 11, 2001, vol. 104, No. 22, pp. 2645-2648.

Wang, Timothy C., et al., "Pancreatic Gastrin Stimulates Islet Differentiation of Transforming Growth Factor a-Induced Ductular Precursor Cells," The Journal of Clinical Investigation, Inc., Sep. 1993, vol. 92, pp. 1349-1356.

Wesley, Umadevi V., et al., "Role for Dipeptidyl Peptidase IV in Tumor Suppression of Human Non Small Cell Lung Carcinoma Cells," Int. J. Cancer, Nov. 2003, 109:855-866.

(56) References Cited

OTHER PUBLICATIONS

Wesley, Umadevi V., et al., "Dipeptidyl Peptidase Inhibits Maignant Phenotype of Prostate Cancer Cells by Blocking Basic Fibroblast Growth Factor Signaling Pathway," Cancer Res. Feb. 25, 2005, a65:1325-1334.
Witchel, "Drug-induced hERG Block and Long QT Syndrome," Cardiovascular Therapeutics, 2011, vol. 29, pp. 251-259.
Wu, Aiguo, et al., "Brain and Spinal Cord Interaction: A Dietary Curcumin Derivative Counteracts Locomotor and Cognitive Deficits After Brain Trauma," Neurohabil Neural Repair, May 2011, 25(4):332-342.
XALKORI Package insert, Pfizer Laboratories, revised Feb. 2013, 10 pp.
Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, Jun. 21, 2007, 1162, pp. 9-18.
Yang, Ping, et al., "Allelic Variants in Long-QT Disease Genese in Patients with Drug-Associated Rosades de Pointes," Circulation, Apr. 23, 2002, pp. 1943-1948.
Yap, Y. G., et al., "Drug Induced QT Prolongation and Torsades de Pointes," Heart, vol. 89, Nov. 2003, pp. 1363-1372.
Zachariae, U., et al., "Side chain flexabilities in the human ether-a-go-go related potassium channel (hERG) together with matched-pair binding studies suggest a new binding mode for channel blockers," J. Med. Chem., vol. 52 (14),Jan. 2, 2009, pp. 4266-4276.
Zhang, L., et al., "Self-Assembled Lipid—Polymer Hybrid Nanoparticles: A Robust Drug Delivery Platform," ACS Nano, vol. 2:8, Jul. 23, 2008, pp. 1696-1702.
Zhou, et al., "Correction of Defectrive Protein Trafficking of a Mutant HERG Potassium Channel in Human Long QT Syndrome," The Journal of Biological Chemistry, vol. 274:44, Oct. 29, 1999, pp. 31123-31126.
Zhou, L., et al., "Nilotinib for Imatinib-Resistant or -Intolerant Chronic Myeloid Leukemia in Chronic Phase, Accelerated Phase, or Blast Crisis: A Single- and Multiple-Dose, Open-Label Pharmacokinetic Study in Chinese Patients," Clinical Therapeutics, vol. 31:7, Jul. 2009, pp. 1568-1575.
Extended European Search Report and Europeean Search Opinion for EPO 10832224.9 dated Feb. 26, 2013, 5 pages.
Extended and Supplemental European Search Report for EPO 11760055.1 dated Jun. 13, 2014, 7 pages.
Extended European Search Report and Europeean Search Opinion for EPO 12757689.0 dated Oct. 22, 2014, 7 pages.
Extended European Search Report and European Search Opinion for 12792560.0 dated Oct. 30, 2014, 11 pages.
International Search Report and Written Opinion for PCT/US2010/057332, dated Aug. 2, 2011, 12 pages.
International Search Report and Written Opinion for PCT/US2011/029393, dated Jun. 23, 2011, 17 pages.
International Search Report and Written Opinion for PCT/US2012/029230, dated Sep. 21, 2012, 14 pages.
International Search Report and Written Opinion for PCT/US2012/040637, dated Dec. 12, 2012, 13 pages.
International Search Report and Written Opinion for PCT/US2013/045898, dated Sep. 6, 2013, 12 pages.
International Search Report and Written Opinion for PCT/US2014/071246, dated Mar. 27, 2015, 14 pages.
International Search Report and Written Opinion for PCT/US2015/034078, dated Aug. 31, 2015, 17 pages.
International Search Report and Written Opinion for PCT/US2013/057744 dated Dec. 12, 2013, 14 pages.
Abel, Ted., et al., "Epigenetic Targets of HDAC Inhibition in Neurodegenerative and Psychiatric Disorders," Current Opinion in Pharmacology, (2008), vol. 8, pp. 57-64.
Aggarwal, et al., "The Molecular Targets and Therapeutic Uses of Curcumin in Health and Disease," (2006), Springer, 515 pages.
Anderson, P., et al., "The Hippocampus Book," Oxford University Press, 2006, 102 pages.
Anderson, Corey, et al., "Most LQT2 Mutations Reduce Kv11.1 (hERG) Current by a Class 2 (Trafficking-Deficient) Mechanism," Circuilation, Nov. 11, 2005, pp. 365-373.
Arbiser, Jack L., et al., "Curcumin is an In Vivo Inhibitor of Angiogenesis," Moledular Medicine, (1998), 4:376-383.
Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.
Bala, Kiran, et al., "Neuroprotective and Anti-Aging Effects of Curcumin in Aged Rat Brain Regions," Biogerontology, (2006), vol. 7, pp. 81-89.
Begum, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.
Bentzen, Peter J., et al., "Curcumin Induced Suicidal Erythrocyte Death," Cellular Physiology and Biochemistry, (2007), 19:153-164.
Bisht, Savita, et al., "Polymeric Nanoparticle-Encapsulated Curcumin ("Nanocurcumin"): A Novel Strategy for Human Cancer Therapy," Journal of Nanobiotechnology, (2007), 18 pages.
Bisht, Savita, et al., "Systemic Administration of Polymeric Nanoparticle-Encapsulated Curcumin (NanoCurcTM) Blocks Tumor Growth and Metastases in Preclinical Models of Pancreatic Cancer," Mol. Cancer Ther., (Aug. 2010), 9(8):2255-2264.
Blomgren, Kerstin, et al., "Obesity and Treatment of Diabetes with Glyburide may Both be Risk Factors for Acute Pancreatitis," Diabetes Care, (2002), 25:298-302.
Brownlee, Michael, "Biochemistry and Molecular Cell Biology of Diabetic Complications," Nature, Dec. 13, 2001, vol. 414, pp. 813-820.
Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, May 31, 2010, 2:43, 11 pages.
Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.
Layton, D, et al., "Prolongation of the QT interval and cardiac arrhythmias associated with cisapride: limitations of the pharmacoepidemiological studies conducted and proposals for the future," Pharmacoepidemiol Drug Saf., 12(1), Nov. 13, 2002, pp. 31-40.
Lee, et al., "Electrophysiological Effects of the Anti-Cancer Drug Lapatinib on Cardiac Repolarization," Basic & Clinical Pharmacology & Toxicology, vol. 107, Dec. 21, 2009, pp. 614-618.
Leung, et al., "Effective stablization of curcumin by association to plasma proteins: human serum albumin and fibronogen," Langmuir, Mar. 25, 2009, vol. 25, Issue 10, pp. 5773-5777.
Li, Lan, et al., "Liposome-Encapsulated Curcumin In Vitro and In Vivo Effects on Proliferation, Apoptosis, Signaling, and Angiogenesis," Cancer, May 4, 2005, 104:1322-1331.
Li, Yu-Cheng, et al., "Antidepressant-Like Effects of Curcumin on Serotonergic Receptor-Coupled Ac-CAMP Pathway in Chronic Unpredictable Mild Stress of Rats," Progress in Neuro-Psychophamacoloby & Biological Psychiatry, Jan. 22, 2009, vol. 33, pp. 435-449.
Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.
Logan-Smith, Melanie J., et al., "Curcumin, a Molecule that Inhibits the Ca2+-ATPase of Sarcoplasmic Reticulum but Increases the Rate of Accumulation of Ca2+," The Journal of Biological Chemistry, Oct. 9, 2001, vol. 276, No. 50, pp. 46905-46911.
Mach, Claire M., et al., "Determination of Minimum Effective Dose and Optimal Dosing Schedule for Liposomal Curcumin in a Xenograft Human Pancreatic Cancer Model," Apr. 2009, Anticancer Research, 29:1895-1900.
Maciel, NR, et al., "Reduced Cardiovascular Alterations of Tarter Emetic Administered in Long-Circulating Liposomes in Rats," Toxicology Letters, Sep. 15, 2010; 199(3):234-238.

(56) References Cited

OTHER PUBLICATIONS

Marino, Silvia, et al., "Sertaline in the Treatment of Depressive Disorders in Patients with Parkinson's Disease," Neurological Sciences, Nov. 2008, 29:391-395.
Matsushita, Yuichi, et al., "Activation of Peroxisome Proliferator-Activated Receptor d Inhibits Streptozotocin-Induced Diabetic Nephropathy Through Anti-Inflammatory Mechanisms in Mice," Diabetes, Mar. 2011, vol. 60, pp. 960-968.
Mayer, Lawrence D., et al., "Intravenous Pretreatment with Empty pH Liposomes Alters the Pharmacokinetics and Toxicity of Doxorubicin through In Vivo Active Drug Encapsulation," Journal of Pharmaceutical Sciences, vol. 88, No. 1, Nov. 25, 1998, pp. 96-102.
Mehta, RT, et al., "Formulation, toxicity, and antifungal activity in vitro of liposomal-encapsulated nystatin as therapeutic agent for systemic candidiasis," Antimicrob Agents Chemother., 31(12), Dec. 1987, pp. 1897-1900.
Mishra, S., et al., "The effect of curcumin (turmeric) on Alzheimer's disease: An overview," Annals of Indian Academy of Neurology, vol. 11:1, 2008, pp. 13-19.
Moha, H, et al., "Curcumin blocks the recombinant human cardiac KCNQ 1/KCNE 1 channels (IKs) stably expressed in HEK 293 cells," Abstract of 12th Annual Meeting of the French Society of Pharmacology and Therapeutics, Fund. & Clin. Pharma., vol. 22:1, Jun. 2008.
Mosse, et al., "Safety and activity of crizotinib for pediatric patients with refractory solid tumours of anaplastic large-cell lymphoma: a Children's Oncology Group phase 1 consortium study," Lancet Oncol., May 2013, vol. 14(6), pp. 472-480.
Mukerjee, Anindita, et al., "Formulation, Characterization and Evaluation of Curcumin-Loaded PLGA Nanospheres for Cancer Therapy," Anticancer Research, Sep. 7, 2009, 29:3867-3876.
Murphy, Eric, A., et al., "Targeted Nanogels: A Versatile Platform for Drug Delivery to Tumors," Molecular Cancer Therapeutics, Apr. 25, 2011; 10:972-982.
Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.
Narala, Venkata R., et al., "Curcumin is not a Ligand for Peroxisome Proliferator-Activated Receptor-Y," Gene Therm. Mol. Biol., Apr. 1, 2009, 13(1):20-25.
Naseem, et al., "Bupivacaine Extended Release Lipsome Injection Does not Prolong Qtc Interval in a Thorough QT/QTc Study in Healthy Volunteers," Journal of Clin. Pharma., 2012, vol. 52, pp. 1441-1447.
National Biodiversity Authority, Secretary of Government of India, Third Party Observation for Application No. EP20110760055, submitted for observation on Jul. 20, 2017, 7 pp.
Nousiainen, T., et al., "QT dispersion and late potentials during doxorubicin therapy for non-Hodgkin's lymphoma," Journal of Internal Medicine, 245, 1999, pp. 359-364.
Olansky, Leann, "Do Incretin-Based Therapies Cause Acute Pancreatitis?" Journal of Diabetes Science and Technology, Jan. 2010, vol. 4, Issue 1, pp. 228-229.
Pisarik, et al., "Reduction of free amphothericin B Acute Toxicity in Mice after intravenous administration of empty liposomes," Journal of Infectious Diseases, May 1990, 161(5), pp. 1042-1044.
Pitman, Roger K., et al., "Conceptually Driven Pharmacologic Approaches to Acute Trauma," CNS Spectrums, Feb. 2005, vol. 10, No. 2, pp. 99-106.
Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.
Rajamani, S., et al., "Drug-induced long QT syndrome: hERG K+ channel block and disruption of protein trafficking by fluoxetine and norfluoxetine," British Journal of Pharmacology, Sep. 11, 2006, vol. 149, pp. 481-489.
Rajeswari, A., et al., "Inhibition of monoamine oxidase-B by the polyphenolic compound, curcumin and its metabolite tetrahydrocurcumin, in a model of Parkinson's disease induced by MPTP neurodegeneration in mice," Inflammopharmacology, vol. 16, 2008, pp. 96-99.
Ranjan, A.P., et al., "Efficacy of Liposomal Curcumin in a Human Pancreatic Tumor Xenograft Model: Inhibition of Tumor Growth and Angiogensis," Anticancer Research, vol. 33, No. 9, Jul. 26, 2013, pp. 3603-3609.
Ravindran, J., et al., "Curcumin and Cancer Cells: How Many Ways Can Currly Kill Tumor Cells Selectively?," The AAPS Journal, vol. 11:3, Sep. 2009, pp. 495-510.
Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.
Rodrigues, C., et al., "Derivative Spectrophotmetry as a Tool for the Determination of Drug Partition Coefficients in water/dimyristoyl-L-$\alpha$-phosphatidylglycerol (DMPG) Liposomes," Biophysical Chemistry, Sep. 2001; 94:97-106.
Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, Jun. 2005, vol. 134, pp. 671-676.
Rui, Pan, et al., "Curcumin Improves Learning and Memory Ability and its Neuroprotective Mechanism in Mice," Chin. Med. J., Jan. 2008, vol. 121, No. 9, pp. 832-839.
Rusinek, Henry, et al., "Hippocampal Blood Flow in Normal Aging Measured with Arterial Spin Lavelin at 3T," Magnetic Resonance in Medicine, Oct. 11, 2011, 65:128-137.
Schena, Francesco P., et al., "Pathogenetic Mechanisms of Diabetic Nephropathy," J. Am. Soc. Nephrol., (2005), 16:330-S33.
Segman, RH., et al., "Association Between the Dopamine Transporter Gene and Posttraumatic Stress Disorder," Molecular Psychiatry, (2002), vol. 7, pp. 903-907.
Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.
Shah, et al., "Cardiovascular Safety of Tyrosine Kinase Inhibitors: With a Special Focus on Cardiac Repolarisation (QT Interval)," Drug Saf., Apr. 26, 2013, vol. 36, pp. 295-316.
Shaikh, J., et al., "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.
Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, Mar. 16, 2000, 102:706-712.
Shimizu, Wataru, et al., "Sodium Channel Block with Mexiletine is Effective in Reducing Dispersion of Repolarization and Preventing Torsade de Pointes in LQT2 and LQT3 Models of the Long-QT Syndrome," vol. 96, Apr. 28, 1997, pp. 2038-2047.
Singh, Sonal, et al., "Long-Term Risk of Cardiovascular Events with Rosiglitazone," JAMA, Sep. 12, 2007, vol. 298, No. 10, pp. 1189-1195.
Smith, Judith A., et al., "Abstract A29: Development of Liposomal Curcumin as a New Potential Anticancer Agent," Molecular Cancer Therapeutics, Dec. 2009, vol. 8, Issue 12, Supplement 1, 1 page.
Stansfeld, Phillip, J., et al., "Drug Block of the hERG Potassium Channel: Insight From Modeling," Proteins: Structure, Function and Bioinformatics, Apr. 19, 2007, 68:568-580.
Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.
Sun, M., et al., "Enhancement of transport of curcumin to brain in mice by poly(n-butylcyanoacrylate) nanoparticle," J. Nanopart Res., vol. 12, Apr. 2010, pp. 3111-3122.
Chao, Chun C., et al., "Glia: The Not So Innocent Bystanders," Journal of NeuroVirology, Apr. 1996, 2:234-239.
Chen, Shali, et al., "High glucose-induced, endothelin-dependent fibronectin synthesis is mediated via NF-κB and AP-1," Am J. Physiol. Cell Physiol., Sep. 18, 2002, 284:C263-C272.

(56) References Cited

OTHER PUBLICATIONS

Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.
Chiu, Jane, et al., "Curcumin Prevents Diabetes-Associated Abnormalities in the Kidneys by Inhibiting p300 and Nuclear Factor-κB," Nutrition, (2009), 25:964-972.
Compton, SJ, et al., "Genetically Defined Therapy of Inherited Long-QT Syndrome. Correction of Abnormal Repolarization by Potassium," Circulation, 1996; 94:1018-1022.
Crack, Peter J., et al., "Glutathione Peroxidase-1 Contributes to the Neuroprotection Seen in the Superoxide Dismutase-1 Transgenic Mouse in Response to Ischemia/Reperfusion Injury," Journal of Cerebral Blood Flow and Metabolism, Aug. 2002, vol. 23, No. 1, pp. 19-22.
Crouch, et al., "Clinical Relevance and Management of Drug-Related QT Interval Prolongation," Pharmacotherapy, Nov. 7, 2003, vol. 23:7, pp. 881-908.
D'Amico, Michele, et al., "Long-Term Inhibition of Dipeptidyl Peptidase 4 in Alzheimer's Prone Mice," Experimental Gerontology 45,3, Dec. 2009, 24 pp.
Dhule, S.S., et al., "The Combined Effect of Encapsulating Curcumin and C6 Ceramide in Liposomal Nanoparticles against Osteosarcoma," Molecular Pharmaceutics, vol. 11, No. 2, Dec. 31, 2013, pp. 417-427.
Djeddi, D, et al., "A: Effect of Domperidone on QT Interval in Neonates," J Pediatrics, May 2008; 153(5):596-598.
Doherty, K., et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.
Ducroq, J, et al., "Printemps R, Le Grand M.: Additive Effects Ziprasidone and D,L-Sotalol on the Action Potential in Rabbit Purkinje Fibers and on the hERG Potassium Current," J.Pharmacol. Toxicol Methods, 2005; 52:115-122.
Etheridge, SP, et al., "A New Oral Therapy for Long QT Syndrome: Long Term Oral Potassium Improves Repolarization in Patients with hERG Mutations," J Am Coll Cardiol, Jul. 2003; 42:1777-1782.
Everett, Peter C., et al., "Preclinical Assessment of Curcumin as a Potential Therapy for B-CLL," American Journal of Hematology, (2006), 8 pp.
Extended European Search Report and Europeean Search Opinion for EPO 10832224.9 dated Feb. 26, 2013, 5 pp.
Extended and Supplemental European Search Report for EPO 11760055.1 dated Jun. 13, 2014, 7 pp.
Extended European Search Report and Europeean Search Opinion for EPO 12757689.0 dated Oct. 22, 2014, 7 pp.
Extended European Search Report and European Search Opinion for 12792560.0 dated Oct. 30, 2014, 11 pp.
Fahn, Stanlex, "Medical Treatment of Parkinson's Disease," Journal of Neurology, 1998, 245 (Supplement 3): p. 15-p. 24.
Fauchier, L, et al., "JP: Effect of Verapamil on QT Interval Dynamicity," Am J Cardiol., Mar. 1, 1999; 83(5):807-808 A10-1.
FDA Pharmacology Review of Xalkori (crizotinib), IND No. 202570, 2011a, www.accessdata.fda.gov/drugsatfda_docs/nda/2011/202570Orig1s000PharmR.pdf (accessed Oct. 9, 2013).
FDA Pharmacology of Tasigna® (nilotinib), IND No. 22-068, 2007a, www.accessdata.fda.gov/drugsatfda_docs/nda/2007/022068s000_PharmR_P1.pdf and www.accessdata.fda.gov/drugsatfda_docs/nda/2007/022068s000_MedR_P2.pdf, (accessed Oct. 25, 2013).
Fowler, NO et al., "Electrocardiogram Changes and Cardiac Arrhythmias in Patients Receiving Psychotropic Drugs," Am J Cardiol, Jul. 1976; 37(2):223-230.
Garcia-Alloza, M., et al., "Curcumin Labels Amyloid Pathology in Vivo, Disrupts Existing Plaques, and Partially Restroes distorterneurites in an Alzheimer Mouse Model," Journal of Neurochemistry, Mar. 2007, vol. 102, pp. 1095-1104.
Gou, M., et al., "Curcumin-loaded biodegradable polymeric micelles for colon cancer therapy in vitro and in vivo," Nanoscale, vol. 3, No. 4, Oct. 2010, pp. 1558-1567.
Grama, C.N., et al., "Poly(lactide-glycolide) nanoparticles for peroral delivery of bioactives," Current Opinion in Colloid and Interface Science, London, GB, vol. 16, No. 3, Nov. 24, 2010, pp. 238-245.
Gukovsky, Ilya, et al., "Curcumin Ameliorates Ethanol and Nonethanol Experimental Pancreatitis," Am. J. Physiol. Gastrointest. Liver Physiol., Oct. 2002, 284:G85-G95.
Harish, G., et al., "Bioconjugates of curcumin display improved protection against glutathione depletion mediated oxidative stress in a dopaminergic neuronal cell line: Implications for Parkinson's disease," Bioorgaic & Medicinal Chemistry, vol. 18, Feb. 20, 2010, pp. 2631-2638.
Helson, et al., "Liposome mitigation of curcumin inhibition of cardiac potassium delayed-rectifier current," Journal of Receptor, Ligand and Channel Research, Nov. 15, 2012, vol. 5, pp. 108.
Hernandez-Fonseca, Juan P., et al., "Structural and Ultrastructural Analysis of Cerebral Cortex, Cerebellum, and Hypothalamus from Diabetic Rats," Experimental Diabetes Research, Oct. 1, 2009: 329632.
International Search Report and Written Opinion for PCT/US2015/034078, dated Aug. 31, 2015, 17 pp.
Jacob, Asha, et al., "Mechanism of the Anti-Inflammatory Effect of Curcumin: PPAR-y Activation," Hindawi Publishing Corporation, PPAR Research, Nov. 2007, Article ID 89369, 5 pages.
Jervell, A, et al., "Congenital Deaf-Mutism, Functional Heart Disease with Prolongation of the QT Interval and Sudden Death," Am Heart J., Jul. 1957; 54(1):59-68.
Kang, J, et al., "Discovery of a Small Molecule Activator of the Human Ether-a-go-go—Related Gene(HERG) Cardiac K+ Channel," Mol Pharmacol, 2005(3); 67-827-836.
Katchman, AN, et al., "Comparative Evaluation of HERG Currents and QT Intervals Following Challenge with Suspected Torsadogenic and Nontorsdogenic Drugs," J Pharmacol Exp Ther., 2006; 316(3):1098-1106.
Kessler, Ronald C., et al., "Posttraumatic Stress Disorder in the national Comorbidity Survey," Archives of General Psychiatry, vol. 52, No. 12, Dec. 1995, pp. 1049-1060.
Kim, K-P., et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.
Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.
Koehler, Jacqueline A., et al., "Glucagon-Like Peptide-1 Receptor Activation Modulates Pancreatitis-Associated Gene Expression Bud Does Not Modify the Susceptibility to Experimental Pancreatitis in Mice," Diabetes, Sep. 2009, vol. 58, pp. 2148-2161.
Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.
Kourelis, Taxiarchis V., et al., "Metformin and Cancer: New Applications for an Old Drug," Med. Oncol., Feb. 8, 2011, 14 pages.
Kowluru, Renu A., et al., "Effects of Curcumin on Retinal Oxidative Stress and Inflammation in Diabetes," Nutrition & Metabolism, Apr. 16, 2007, 8 pages.
Kulkarni, S.K., et al., "An Overview of Curcumin in Neurological Disorders," Indian J. Pharm. Sci, Jul. 1, 2010, 72:2, pp. 149-154.
Chartrand, et al., "Potential role of the membrane in hERG channel functioning and drug-induced long QT syndrome," Biochimica et Biophysica Acta, May 25, 2010, vol. 1798, pp. 1651-1662.
Chayanupatkul "Cirrhotic cardiomyopathy: review of pathophysiology and treatment." Hepatol Int., Jul. 2014, vol. 8, No. 3, pp. 308-315.
Gilenya (Fingolimod) Full Prescribing Information, Novartis: T2016-22, Feb. 2016, 25 pp.
Yagi, Y., et al., "Analysis of Onset Mechanisms of a Sphingosine 1-Phosphate Receptor Modulator Fingolimod-Induced Atrioven- (56) References Cited

OTHER PUBLICATIONS tricular Conduction Block and QT-Interval Prolongation," Toxicology and Applied Pharmacology, Sep. 16, 2014, 281, pp. 39-47.
Zeltser, et al., "Drug-induced atrioventricular block: prognosis after discontinuation of the culprit drug." Journal of the American College of Cardiology, Jul. 2004, vol. 44, No. 1, pp. 105-108.
Gilhotra, N. et al., "GABAergic and nitriergic modulation by curcumin for its antianxiety-like activity in mice," Brain Research 1352 (2010), pp. 167-175.
Xu, Ying, et al., "Curcumin Reverses Impaired Cognition and neuronal plasticity induced by chronic stress," Neuropharmacology, 57.4 (2009), pp. 463-471.
Israelachvilli, JN, et al., "Physical principles of membrane organization," Quarterly Reviews of Biophysics, vol. 13(2), 1980, pp. 121-200.
Webster, G., et al., "Contemporary reviews in cardiovascular medicine, An Update on Channelopathies," Jan. 2013, vol. 127, pp. 126-140.
Lian, T., et al., "Trends and Developments in Liposome Drug Delivery Systems," MiniReview, Journal of Pharmaceutical Sciences, vol. 90, No. 6, Jun. 2001, pp. 667-680.
Chinthalapally, et al., "Inhibition by dietary curcumin of azoxymethane-induced ornithine decarboxylase, tyrosine protein kinase, arachidonic acid metabolism and aberrant crypt foci formation in the rat colon," Carcinogensis, vol. 14, Iss. 11, Nov. 1, 1993, pp. 2219-2225.
Extended European Search Report and European Search Opinion for 15803421.5 dated Nov. 10, 2017.
Hasima, N., et al., "Cancer-linked targets modulated by curcumin," Int. J. Biochem. Mol. Bio., Dec. 30, 2012, vol. 3(4), pp. 328-351.
Hong, et al., "Curcumin inhibits tyrosine kinase activity of p195neu an also depletes p185neu," Clinical Cancer Research, Mar. 22, 1999, 5(7), pp. 1884-1891.
Rawal, et al., "Paclitaxel Induced Acute ST Elevation Myocardial Infarction: A Rare Case Report," Journal of Clinical and Diagnostic Research, Oct. 2016, vol. 10(10), pp. XD01-XD02.
WHO Model List of Essential Medicines, World Health Organization, Oct. 2013. pp. 1-47.
Wikipedia2, https://en.wikipedia.org/wiki/Atrioventricular_block (downloaded on Jul. 26, 2018).
Wong-Beringer, Annie, et al., "Lipid Formulations of Amphotericin B: Clinical Efficacy and Toxicities," Clinical Infectious Diseases, May 4, 1998, vol. 27, pp. 603-618.
International Search Report and Written Opinion of Korean Intellectual Property Office for PCT/US2017/060936 dated Feb. 20, 2018, 13 pp.

* cited by examiner

PREVENTION OF DRUG-INDUCED ATRIO-VENTRICULAR BLOCK

CROSS-REFERENCE TO RELATED APPLICATIONS

This application claims priority to U.S. Provisional Application Ser. No. 62/328,307 filed Apr. 27, 2017, the entire contents of which are incorporated herein by reference.

TECHNICAL FIELD OF THE INVENTION

The present invention relates in general to the field of drug-induced atrio-ventricular block, and more particularly, to a composition and method for reducing or preventing drug-induced atrio-ventricular block.

STATEMENT OF FEDERALLY FUNDED RESEARCH

None.

BACKGROUND OF THE INVENTION

Without limiting the scope of the invention, its background is described in connection with compositions and methods for controlling the duration of repolarization of the cardiac ventricle QT in a subject comprising administering to subject in need thereof of a modification of or functional interference with a therapeutic agent, or congenital defect which, if unmodified, can induce prolongation of repolarization in the heart myocyte action potential, torsade de points, and the long QT syndrome.

The beating of the heart is due to precisely controlled regularly spaced waves of myocardial excitation and contraction. The electrical currents during ion-based depolarization and repolarization can be measured by electrical leads placed on the body in specific locations (the electrocardiogram), which measure electrical waves. The P-wave represents a wave of depolarization in the atrium. When the entire atria becomes depolarized, the wave returns to zero. After 0.1 seconds the ventricle is entirely depolarized resulting in the QRS complex. The three peaks are due to the way the current spreads in the ventricles. This is followed by the T-wave or repolarization of the ventricle. The QT interval measured from the beginning of the QRS complex to the end of the T wave on the standard ECG represents the duration until the completion of the repolarization phase of the cardiac myocyte (or the depolarization and repolarization of the ventricle). The duration of this interval can vary due to genetic variation, cardiac disease, electrolyte balance, envenomation, and drugs. Prolongation of the QT interval, can result in ventricular arrhythmias, and sudden death.

Drug induced long QTc Syndrome (LQTS) i.e., a prolongation of the action potential duration is a common cause of governmental mandated drug withdrawal. QTc prolongation is an unpredictable risk factor for Torsades de Pointes (TdP), a polymorphic ventricular tachycardia leading to ventricular fibrillation. Drug induced LQTS comprises about 3% of all prescriptions which when followed by TdP may constitute a lethal adverse reaction. Patients taking one or more than one QTc-prolonging drug concomitantly, have an enhanced risk of TdP. While the overall occurrence of TdP is statistically rare but clinically significant for the affected individual, assay for this drug effect is a mandatory requirement prior to allowing a drug to enter clinical trials.

Common structurally diverse drugs block the human ether-a-g-go-related gene (KCNH2 or hERG), coded $K^+$ channel and the cardiac delayed-rectifier potassium current $I_K$ (KV11.1) resulting in acquired LQTS. Drug-associated increased risk of LQTS is a major drug development hurdle, and many drugs have been withdrawn during pre-clinical development, or assigned black box warnings following approval or withdrawn from the market. Autosomal recessive or dominant LQTS based upon 500 possible mutations in 10 different genes coding for the potassium channel has an incidence of 1:3000 or about 100,000 persons in the US. Prolonged QT intervals, or risk of LQTS occur in 2.5% of the asymptomatic US population. This syndrome when expressed can lead to severe cardiac arrhythmia and sudden death in untreated patients. The probability of cardiac death in patients with asymptomatic congenital LQTS who are medicated with LQTS-inducing drugs is increased.

The majority of the acquired LTQS drug withdrawals are due to obstruction of the potassium ion channels coded by the human ether-a-go-go related gene (hERG). High concentrations of hERG blocking drugs generally induce a prolonged QTc interval and increase the probability of TdP. Up to 10% of cases of drug-induced TdP can be due to due to 13 major genetic mutations, 471 different mutations, and 124 polymorphisms (Chig, C 2006).

Systems and methods for detection of LQTS have been described previously. For example U.S. Patent Publication No. 2010/0004549 (Kohls et al. 2010) discloses a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patients ECG to these databases will facilitate the detection of such occurrences as changes in QT interval from success of ECGs, changes in T-wave morphology, changes in U-wave morphology and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

A system and method for the diagnosis and treatment of LQTS is described in U.S. Patent Publication No. 20080255464 (Michael, 2008). The Michael invention includes a system for diagnosing Long QT Syndrome (LQTS) derives a QT/QS2 ratio from an electrical systole (QT) and a mechanical systole (QS2) to detect a prolonged QT interval in a patient's cardiac cycle. A processor acquires the systoles from a microphone and chest electrodes, calculates the QT/QS2 ratio, and outputs the result to a display. The processor may compare the QT/QS2 ratio to a threshold value stored in memory for diagnosing LQTS in the patient. A user interface provides for programming, set-up, and customizing the display. A mode selector allows the system to operate alternatively as a phonocardiograph, a 12 lead electrocardiograph, or a machine for diagnosing LQTS. A related method for diagnosing cardiac disorders such as LQTS includes measuring QT and QS2 during a same cardiac cycle, calculating a QT/QS2 ratio, and comparing the result to a threshold value derived from empirical data. The method may include measuring systoles both at rest and during exercise, and may be used for drug efficacy, dosage optimization, and acquired LQTS causality tests.

A method for the treatment of cardiac arrhythmias is provided in U.S. Patent Publication No. 20070048284 (Donahue and Marban, 2007). The method includes administering an amount of at least one polynucleotide that modulates an electrical property of the heart. The polynucleotides of the invention may also be used with a microdelivery vehicle such as cationic liposomes and adenoviral vectors.

SUMMARY OF THE INVENTION

In one embodiment the present invention includes a method of treating a drug-induced atrioventricular (AV) block comprising: providing a subject in need of a drug therapy that is contraindicated to treat a disease or condition in the subject, wherein the drug causes an AV block, with an amount of a lipid sufficient to reduce or eliminate the AV block caused by the drug. In one aspect, the lipid is provided orally, enterally, parenterally, intravenously, or intraperitoneally. In another aspect, the drug is provided orally, enterally, parenterally, intravenously, or intraperitoneally. In another aspect, the drug is defined further as a combination of two or more drugs, wherein each of the drugs individually causes limited or no AV block, but when provided in combination causes a first-, a second-, or a third-degree AV block. In another aspect, the lipid comprises at least one of 1,2-Dimyristoyl-sn-glycero-3-phosphorylcholine (DMPC), 1,2-Dimyristoyl-sn-glycero-3-phosphorylglycerol (DMPG), DMPC/DMPG, 1-Myristoyl-2-Hydroxy-sn-Glycero-3-Phosphocholine, 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), 1-myristoyl-2-hydroxy-sn-glycero-3-phospho-(1'-rac-glycerol) (LysoPG), 1-myristoyl-2-hydroxy-sn-glycero-3-phosphocholine (LysoPC), lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the lipid comprises a phosphatidylglycerol or a lysophosphatidylglycerol defined further as comprising a short chain fatty acid comprising up to 5 carbons, a medium chain is 6 to 12 carbons, a long chain is 13-21 carbons and a very long chain fatty acid is greater than 22 carbons, including both even and odd chain fatty acids. In another aspect, the lipid comprises a phosphatidylglycerol or a lysophosphatidylglycerol has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the drug is Fingolimod, or is a combination of Fingolimod and verapamil. In another aspect, the Fingolimod and verapamil and the liposome comprises at least one of 1,2-Dimyristoyl-sn-glycero-3-phosphorylcholine (DMPC), 1,2-Dimyristoyl-sn-glycero-3-phosphorylglycerol (DMPG), DMPC/DMPG, 1-Myristoyl-2-Hydroxy-sn-Glycero-3-Phosphocholine, 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), 1-myristoyl-2-hydroxy-sn-glycero-3-phosphocholine (LysoPC) and the reduction in AV block is at least 50, 60, 70, 7, 80, 85, 90, 95, or 100%. In another aspect, the lipid are provided orally and the AV block is reduced or prevented for at least one, two, four, six or eight hours. In another aspect, the AV block is a third-degree AV block that is reduced or eliminated. In another aspect, the lipid forms a liposome, and optionally the liposome is empty. In another aspect, the lipid is formulated for at least one of: immediate, intermediate, or extended release.

Yet another embodiment of the present invention includes a method of treating a drug-induced atrioventricular (AV) block comprising: identifying a subject in need for a therapeutic treatment with a drug, wherein the drug causes AV block as a side effect and the drug is contraindicated for that subject; and providing an effective amount of a lipid sufficient to eliminate the drug-induced AV block. In one aspect, the lipid is provided orally, enterally, parenterally, intravenously, or intraperitoneally. In another aspect, the drug is provided orally, enterally, parenterally, intravenously, or intraperitoneally. In another aspect, the drug is defined further as a combination of two drugs, wherein each of the drugs individually causes limited or no AV block, but when provided in combination causes an AV block. In another aspect, the lipid comprises at least one of 1,2-Dimyristoyl-sn-glycero-3-phosphorylcholine (DMPC), 1,2-Dimyristoyl-sn-glycero-3-phosphorylglycerol (DMPG), DMPC/DMPG, 1-Myristoyl-2-Hydroxy-sn-Glycero-3-Phosphocholine, 1-myristoyl-2-hydroxy-sn-glycero-3-phospho-(1'-rac-glycerol) (LysoPG), 12-Mysteroyl-2-Hydroxy-sn-Glycero-3-[Phospho-rac-(glycerol)], 1-myristoyl-2-hydroxy-sn-glycero-3-phosphocholine (LysoPC), lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the lipid comprises a phosphatidylglycerol or a lysophosphatidylglycerol defined further as comprising a short chain fatty acid is up to 5 carbons, a medium chain is 6 to 12 carbons, a long chain is 13-21 carbons and a very long chain fatty acid is greater than 22 carbons, including both even and odd chain fatty acids. In another aspect, the lipid comprises a phosphatidylglycerol or a lysophosphatidylglycerol has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the drug is Fingolimod, or is a combination of Fingolimod and verapamil. In another aspect, the Fingolimod and verapamil and the liposome comprises at least one of 1,2-Dimyristoyl-sn-glycero-3-phosphorylcholine (DMPC), 1,2-Dimyristoyl-sn-glycero-3-phosphorylglycerol (DMPG), DMPC/DMPG, 1-Myristoyl-2-Hydroxy-sn-Glycero-3-Phosphocholine, 1-myristoyl-2-hydroxy-sn-glycero-3-phospho-(1'-rac-glycerol) (LysoPG), 1-myristoyl-2-hydroxy-sn-glycero-3-phospho-(1'-rac-glycerol) (LysoPG), or 1-myristoyl-2-hydroxy-sn-glycero-3-phosphocholine (LysoPC) and the reduction in AV block is at least 50, 60, 70, 7, 80, 85, 90, 95, or 100%. In another aspect, the AV block is a third-degree AV block that is reduced or eliminated. In another aspect, the lipid is formulated for at least one of: immediate, intermediate, or extended release. In another aspect, the lipid is a liposome, and optionally the liposome is empty.

Yet another embodiment is a method of evaluating a candidate drug believed to be useful in eliminating a drug-induced atrioventricular (AV) block, the method comprising: a) measuring the extent of AV block caused by a drug suspected of causing AV block alone or in combination from a first set of patients; b) administering a candidate drug to a first subset of the patients, wherein the candidate drug is a lipid, and a placebo to a second subset of the patients; c) repeating step a) after the administration of the candidate drug or the placebo; and d) determining if the candidate drug reduces the AV block caused by the drug that is statistically significant as compared to any reduction occurring in the second subset of patients, wherein a statistically significant reduction indicates that the candidate drug is useful to reduce or prevent an AV block caused by the drug. In one aspect, the candidate agent is a lipid, and optionally, the lipid forms a liposome, and optionally the liposome is empty.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises providing a lipid that inhibits atrioventricular block (AV Block), which lipid can be provided prior to the AV Blocking drug by, e.g., oral, parenteral (intravenous or subcutaneous) administration, or the lipid may be provided as an empty liposome prior to or concomitantly with therapeutic agents known to have a high risk of AV Block.

The term "lipid" refers to lipids, for example, phospholipids, with the optional addition therewith of a sterol, especially cholesterol. The lipids can be provided alone or in combination with other lipids, can be saturated and unsaturated, branched or unbranched, can be in the form of a lipid tri-glycerol molecule. Non-limiting examples of lipids for use with the present invention include but are not limited to, e.g., 1,2-Dimyristoyl-sn-glycero-3-phosphorylcholine (DMPC), 1,2-Dimyristoyl-sn-glycero-3-phosphorylglycerol (DMPG), 1-Myristoyl-2-Hydroxy-sn-Glycero-3-Phosphocholine, DMPC/DMPG, 1-myristoyl-2-hydroxy-sn-glycero-3-phospho-(1'-rac-glycerol) (LysoPG), 1-myristoyl-2-hydroxy-sn-glycero-3-phospho-(1'-rac-glycerol) (LysoPG), 1-myristoyl-2-hydroxy-sn-glycero-3-phosphocholine (LysoPC), lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. Following the guidance of the present invention, other lipids can be identified that have the claimed function as taught herein without undue experimentation.

The term "liposome" refers to a capsule wherein the wall or membrane thereof is formed of lipids, especially phospholipid, with the optional addition therewith of a sterol, especially cholesterol. In one specific non-limiting example the liposomes are empty liposomes and can be formulated from a single type of phospholipid or combinations of phospholipids. The empty liposomes can further includes one or more surface modifications, such as proteins, carbohydrates, glycolipids or glycoproteins, and even nucleic acids such as aptamers, thio-modified nucleic acids, protein nucleic acid mimics, protein mimics, stealthing agents, etc. In one embodiment, the liposome is a liposome or a liposome precursor comprising, e.g., a LysoPG, a myristoyl monoglyceride, and a myristic acid. In one specific, non-limiting example the composition also comprises an active agent in or about the liposome and the composition has a ratio of phospholipids to active agent of 3:1, 1:1, 0.3:1, and 0.1:1.

As used herein, the term "in vivo" refers to being inside the body. The term "in vitro" used as used in the present application is to be understood as indicating an operation carried out in a non-living system.

As used herein, the term "receptor" includes, for example, molecules that reside on the surface of cells and mediate activation of the cells by activating ligands, but also is used generically to mean any molecule that binds specifically to a counterpart. One member of a specific binding pair would arbitrarily be called a "receptor" and the other a "ligand." No particular physiological function need be associated with this specific binding. Thus, for example, a "receptor" might include antibodies, immunologically reactive portions of antibodies, molecules that are designed to complement other molecules, and so forth. Indeed, in the context of the present invention, the distinction between "receptor" and "ligand" is entirely irrelevant; the invention concerns pairs of molecules, which specifically bind each other with greater affinity than either binds other molecules. However, for ease of explanation, the invention method will be discussed in terms of target receptor (again, simply a molecule for which a counterpart is sought that will react or bind with it) and "ligand" simply represents that counterpart.

As used herein, the term "treatment" refers to the treatment of the conditions mentioned herein, particularly in a patient who demonstrates symptoms of the disease or disorder.

As used herein, the term "treatment" or "treating" refers to any administration of a compound of the present invention and includes (i) inhibiting the disease in an animal that is experiencing or displaying the pathology or symptomatology of the diseased (i.e., arresting further development of the pathology and/or symptomatology); or (ii) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The terms "effective amount" or "therapeutically effective amount" described herein means the amount of the subject compound that will elicit the biological or medical response of a tissue, system, animal or human that is being sought by the researcher, veterinarian, medical doctor or other clinician.

The terms "administration of" or "administering a" compound as used herein should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

As used herein the term "intravenous administration" includes injection and other modes of intravenous administration.

The term "pharmaceutically acceptable" as used herein to describe a carrier, diluent or excipient must be compatible with the other ingredients of the formulation and not deleterious to the recipient thereof.

Prevention of Drug-Induced QT Prolongation by Lipids.

As is well-known, QTc interval prolongation can degenerate into polymorphic ventricular arrhythmias or Torsades de Pointes. QTc interval prolongation has consistently been one of the most frequent causes of failure in drug development, being responsible for limiting drug prescription or altogether drug withdrawal for over 180 formerly successful drugs.

Lipids and liposomes have been shown to prevent heart rate-corrected QT (QTc) interval prolongation when given simultaneously with a QT-prolonging drug. While the mechanism of action of the lipids and/or liposomes are still under investigation (and are not a limitation of the present invention), the present inventors have found that the lipids and/or liposomes rescue ventricular repolarization by preventing the increase in sarcolemmal membrane rigidity associated with QTc prolongation. Indeed, the flexibility of the channel's pore opening plays a major role in its activation kinetics, and depends on the surrounding lipid environment. When drugs, disease, or other challenges increase ceramide levels in the sarcolemmal membrane, the rigidity of the membrane increases and the hERG channels exhibit slower activation kinetics. There results a decreased reserve of repolarization, and QTc intervals prolong.

Prior work from the present inventors has demonstrated that formulation with a liposome containing 1,2-Dimyristoyl-sn-glycero-3-phosphorylcholine (DMPC), 1,2-Dimyristoyl-sn-glycero-3-phosphorylglycerol (DMPG), DMPC/DMPG, 1-Myristoyl-2-Hydroxy-sn-Glycero-3-Phosphocholine, 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), or 1-myristoyl-2-hydroxy-sn-glycero-3-phosphocholine (LysoPC), lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine, prevented hERG channel inhibition by curcumin. Curcumin is a strong hERG inhibitor and QTc-prolonging agent. The liposomal elimination or reduction of QTc prolongation caused by Curcumin has been pursued successfully through preclinical testing, and into clinical development. To date, 45 normal subjects and 28 cancer patients have been tested in Phase 1a and 1b (ongoing) studies, respectively. Volunteers and patients have demonstrated excellent tolerance to both the curcumin moiety and the liposome incorporated into the clinical-study formulation, without signs of QTc prolongation.

More than 15 QTc-prolonging drugs have had their QTc prolongation eliminated in various regulatory-validated preclinical models, and development is on a fast-track to demonstrate that Moxifloxacin, the current clinical standard for QTc prolongation, does not induce QT prolongation in humans receiving concomitant doses of the lipids. Briefly, guinea pigs were instrumented with ECG leads, and administered increasing oral doses of moxifloxacin. Guinea pigs are the preferred species in Europe and Canada for QT prolongation testing, because they possess a complement of cardiac ion channels most similar to that of humans, and are exquisitely sensitive to proarrhythmic drugs. On the drug side, Moxifloxacin is the preferred QTc-prolonging positive control drug in Thorough QT (TQT) clinical studies because it causes a dose-dependent QTc prolongation in all species, and exhibits very linear pharmacokinetics, making it easy to dose and relatively safe at sub-toxic exposure levels.

Those guinea pigs administered only moxifloxacin exhibited severe (+10 ms) and life-threatening (+30 ms) QTc prolongation. In contrast, those animals that had received a concomitant dose of, as an example, 14:0 lyso PG, exhibited no, or very little, changes in QTc. There resulted a statistically significant right-shift in the QTc-dose response of Moxifloxacin, actually preventing the QTc prolongation from becoming dose-limiting.

Figure 1:
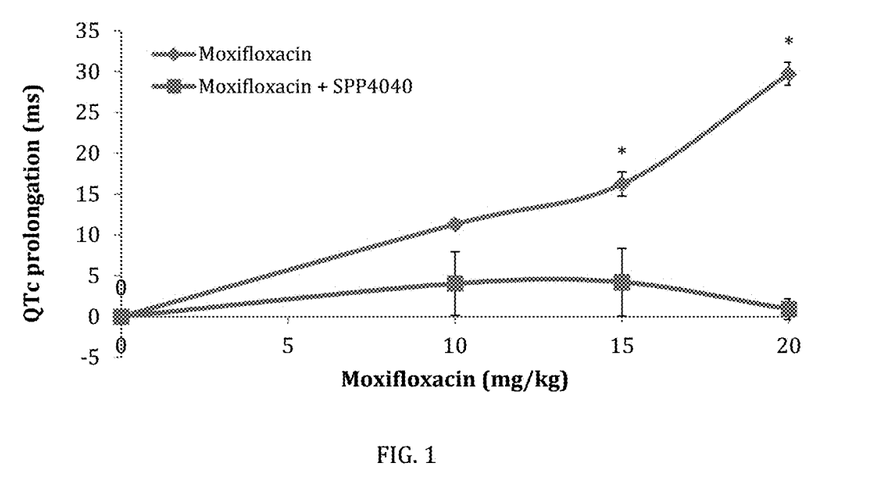
FIG. 1 is a graph that shows the effect of a single oral dose of Moxifloxacin on QTc interval of guinea pigs (Moxiflaxin—diamonds, Moxiflaxin+14:0 lyso PG—squares).

FIG. 1 is a graph that shows the effect of a single oral dose of Moxifloxacin on QTc interval of guinea pigs. Increasing doses of Moxifloxacin were administered orally to instrumented guinea pigs (n=6) either without (diamond) or with (square) concomitant oral administration of 14:0 lyso PG (labeled SPP4040) at a 14:0 lyso PG:Moxifloxacin ratio of 0.45:1. ECGs were recorded at 1, 2, 4, 6 hours post-dose (2-hrs post-dose data are presented).

Through the same effect on membrane fluidity, 14:0 lyso PG prevents the changes in ionic channel activation/inactivation kinetics which lead to QTc prolongation by the following drugs: Moxifloxacin; Nilotinib; Crizotinib; Sotalol; Curcumin; Nifedipine; Lovastatin; Thioridazine; Amiodarone; Terfenadine; E4031; Felbamate; Gilenya; Quizartinib (AC220); Forskolin; and Turmerone, among others.

GILENYA® (Fingolimod) represents an interesting case as pertains to QTc prolongation: Administered alone in healthy, naive animals and clinical volunteers, it causes limited QT/QTc prolongation: delays in repolarization reportedly reached 60 ms at therapeutic doses in a pair of individuals, but mostly remained well below the regulatory threshold for proarrhythmic concern (<500 ms in men, <520 ms in women)("EMA Assessment Report", European Medicines Agency, published 17 Feb. 2011, London.). Fingolimod is thus rightfully considered essentially risk-free as far as QTc prolongation is concerned.

However, clinical patients taking the anti-hypertensive verapamil along with Fingolimod exhibit severely prolonged QTc intervals, to the point where Fingolimod has to be discontinued immediately in those patients. So-called drug-drug interactions are not unheard of, and generally represent low frequency events; unfortunately, verapamil use is extremely common: it is on the World Health Organization's List of Essential Medicines, listing the most important medications needed in a basic health system ("WHO Model List of Essential Medicines" (PDF). World Health Organization. October 2013).

As for Fingolimod, verapamil at a normal therapeutic dose (240 mg/day, approx. 16 µg/mL plasma) does not cause QT/QTc prolongation in healthy volunteers or naive animals. It is well-known that verapamil decreases calcium and potassium ionic currents, and this results in a decrease in the so-called "reserve of repolarization" of patients, a term coined by Dan Roden in 1998, which refers to the redundant processes supporting cardiac electrophysiological timing (Roden D M. Taking the idio out of idiosyncratic: predicting torsades de pointes. Pacing Clin. Electrophysiol. 1998; 21:1029-1034). As per this model of reserve of repolarization, the redundancy built into the cardiac system is such that inhibiting an ionic current (as does verapamil) does not necessarily lead to changes in QTc intervals. An added challenge, however benign, reveals the extent of the otherwise hidden impairment. In verapamil-treated patients, Fingolimod—causing approximately 64% IKr inhibition—has more effect than the reduced reserve of repolarization system can correct for, and QTc prolongation ensues.

Thus, a series of studies were conducted to reproduce clinical reports of verapamil+Fingolimod QTc prolongation, guinea pigs were instrumented with subcutaneous ECG leads before being administered Fingolimod, verapamil, 14:0 lyso PG, or a combination of these. ECGs were recorded continuously, but are illustrated below (FIG. 2) at two (2) hour post dose. QT intervals were measured and corrected individually to yield QTc intervals (ms).

Figure 2:
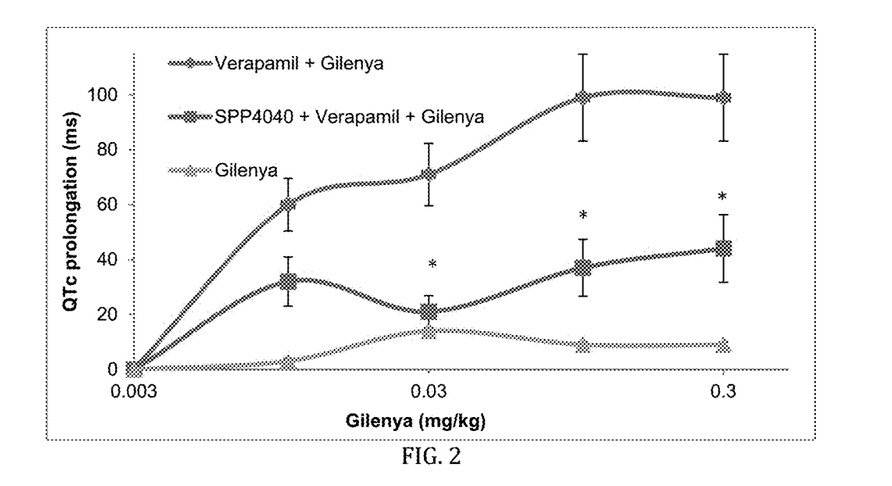
FIG. 2 is a graph that shows the effect of Fingolimod, Verapamil, and 14:0 lyso PG on QTc interval in instrumented guinea pigs (Verapamil+Fingolimod—diamonds, 14:0 lyso PG+Verapamil+Fingolimod—squares, Fingolimod alone—triangles).

FIG. 2 is a graph that shows the effect of Fingolimod, Verapamil, and 14:0 lyso PG (labeled SPP4040) on QTc interval in instrumented guinea pigs. Fingolimod was administered intravenously to instrumented guinea pigs at doses ranging from 3 µg/kg to 300 µg/kg (n=6, green series, above). The intravenous route of administration was selected because it simplified the pharmacokinetics of this multi-drug study.

Another series of animals received 0.5 mg/kg verapamil intravenously at T=0, then were given the same doses of Fingolimod 60 minutes later (n=6, diamond, above). Again, the intravenous route of administration for both drugs was selected to simplify the kinetics of the study.

A third group of animals received an oral dose of 1 mg/kg 14:0 lyso PG at time 0 hr, then an intravenous dose of 0.5 mg/kg verapamil at T=60 min, and an intravenous dose of Fingolimod at T=120 minutes (n=6, square, above). Fingolimod alone is the triangle. 14:0 lyso PG requires GI passage to become active, so it was given orally, and reached its maximal efficacy 120 minutes post oral dosing.

Animals receiving Fingolimod alone exhibited a limited, dose-dependent increase in QTc prolongation, which remained below 15 ms through the range of dose administered. This was in agreement with reported results of fingolimod administration in preclinical models (Yagi, et al. 2014).

When the guinea pigs were administered 0.5 mg/kg verapamil 60 minutes prior to receiving the same doses of Fingolimod, on the other hand, they consistently exhibited extremely prolonged QT/QTc intervals upon Fingolimod administration. Two (2) out of six animals receiving 0.3 mg/kg Fingolimod exhibited polymorphic ventricular tachycardia which degenerated to ventricular fibrillation and death. This was expected based on the clinical reports of severe QTc prolongation in clinical patients taking verapamil and receiving Fingolimod prior to the latter being discontinued due to QTc prolongation.

The outcome of the experiments performed on the third cohort/group was of particular interest: The animals received an oral dose of 1.0 mg/kg 14:0 lyso PG. They exhibited no change in cardiac electrophysiology (the Maximum Tolerated Dose (MTD) for 14:0 lyso PG is greater than the highest achievable dose in the oral formulation used for the gavage in these experiments). Sixty (60) minutes later, the intravenous administration of 0.5 mg/kg verapamil failed to alter ventricular repolarization kinetics: no change in QTc was recorded. Another 60 minutes later, Fingolimod was administered to the 14:0 lyso PG+verapamil animals: the QTc prolongation for any given dose of Fingolimod was measured at less than one third (⅓) that which had been measured in verapamil+Fingolimod animals, suggesting that 14:0 lyso PG right-shifted the QTc prolongation curve in animals impaired with verapamil prior to being administered Fingolimod.

Prevention of Fingolimod-Induced Atrio-Ventricular Block by 14:0 Lyso PG.

Atrioventricular (AV) block is a limitation in electrical conduction between the atria and ventricles of the heart. In an AV block, the depolarizing wave, which normally travels from the sinoatrial (SA) node to the AV node and on to the ventricles, cannot not reach the ventricles or is impaired along the way. While most mild (first and second-degree) AV blocks result from cardiac disease, severe second-degree and third-degree AV blocks are generally caused by drugs (e.g.; beta-blockers, calcium channel blockers, verapamil, digoxin, amiodarone, etc.)(Mitchell, L. B. Atrioventricular Block. The Merck Manual—Professional Version 2015. Merck & Co., Inc., Kenilworth, N.J., USA.). First and second-degree AV blocks are considered asymptomatic: akin to the reduction in reserve of repolarization mentioned in the section above, AV blocks are not in themselves life-threatening. However, they can lead to bradycardia, loss of cardiac output, syncope, exacerbation of underlying cardiac impairment, and ischemic heart disease.

AV block represents an interesting conundrum in cardiology: drug-induced AV block patients are not treated by pacemaker implantation, unlike patients suffering from disease-induced AV block. Yet, there is evidence that drug-induced AV block is irreversible after drug discontinuation in 56% of cases (Zeltser D, Justo D, Halkin A, et al. Drug-induced atrioventricular block: prognosis after discontinuation of the culprit drug. J Am Coll Cardiol. 2004; 44(1):105-108). Current practice is to immediately discontinue AV blocking drugs upon discovering the effect. This withdraws useful, efficient drugs from the pharmacopeia available to oncologists, while directly impacting drug adoption in the clinic.

The ionic channels involved in AV block and QTc prolongation are completely distinct: sodium ($Na^+$) and calcium ($Ca^2$) channel inhibition are responsible for the onset of AV block, while delays in repolarization due to potassium ($K^+$) inhibition lead to QTc prolongation. Yet, the hypothesized mechanism by which lipids rescues K$^+$ currents could also benefit Na$^+$ and Ca2+ currents.

To test this hypothesis, guinea pigs were instrumented (subcutaneous ECG leads) and exposed to increasing intravenous doses of Fingolimod and/or verapamil, without and with an oral dose of 14:0 lyso PG. ECG signals were recorded continuously for 2 hours post-dose for the AV blockers Fingolimod and verapamil. PR intervals were measured following the infusion of Fingolimod. Measurements of PR were stopped when the P wave disconnected from the QRS complexes, indicating 3rd degree AV block.

Guinea pigs exposed to an intravenous infusion of Fingolimod alone transitioned to 1st degree AV block as of a dose of 15 µg/kg, which rapidly progressed to a Mobitz Type-1, 2nd-degree AV block at 20 µg/kg, and finally progressed to 3rd degree AV block as of a dose of 23 µg/kg. The progression of the AV block was rapid and irreversible: stopping infusion did not prevent the onset of P-QRS dissociation.

The cohort of guinea pigs exposed to verapamil received an i.v. injection of 0.5 mg/kg, followed 60 minutes later by an intravenous infusion of Fingolimod. A 1st-degree AV block appeared at a dose of 7 µg/kg, changed to a Mobitz-Type-1 2nd degree AV block at 10 µg/kg, and transitioned to 3rd-degree dissociation between P waves and QRS complexes as of 45 µg/kg.

The third cohort of animals received an initial oral gavage of 1.0 mg/kg 14:0 lyso PG, followed 60 minutes later by an intravenous dose of 0.5 mg/kg verapamil. Sixty (60) minutes post-verapamil, Fingolimod was infused into the animals as described above. The animals exhibited modest changes in PR intervals up to a dose of 200 µg/kg, at which point a 1s-degree AV block appeared. A Mobitz-Type-2 AV block appeared in 2 out of 6 animals with P-QRS dissociation observed at a dose of 51 µg/kg in those two animals, and at 300 µg/kg in the rest of the animals in the cohort.

Figure 3:
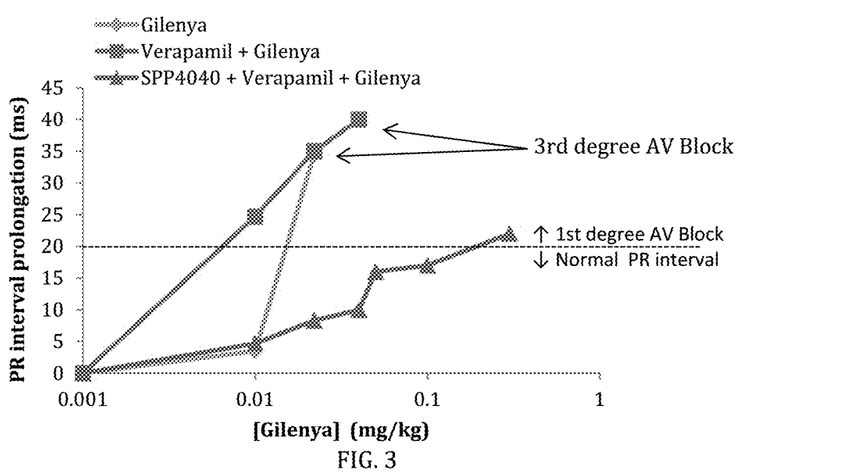
FIG. 3 is a graph that shows the effect of Fingolimod, Verapamil, and 14:0 lyso PG on PR intervals in instrumented guinea pigs (Verapamil+Fingolimod—squares, 14:0 lyso PG+Verapamil+Fingolimod—triangles, Fingolimod alone—diamonds).

FIG. 3 is a graph that shows the effect of Fingolimod, Verapamil, and 14:0 lyso PG (labeled SPP4040) on PR intervals in instrumented guinea pigs. Fingolimod was administered by intravenous infusion to instrumented guinea pigs at doses ranging from 3 µg/kg to 300 µg/kg (n=6, green series, above). The intravenous route of administration was selected because it simplified the pharmacokinetics of this multi-drug experiment.

Another cohort of animals received 0.5 mg/kg verapamil intravenously at T=0, then were given the same doses of Fingolimod 60 minutes later (n=6, blue series, above). Again, the intravenous route of administration for both drugs was selected to simplify the kinetics of the experiment.

A third cohort of animals received an oral dose of 1 mg/kg 14:0 lyso PG at time 0 hr, then an intravenous dose of 0.5 mg/kg verapamil at T=60 min, and an intravenous infusion of Fingolimod starting at T=120 minutes (n=6, red series, above).

It was found that, 14:0 lyso PG, when given orally prior to Fingolimod and/or verapamil, right-shifted the appearance of 3rd-degree AV block by 13-fold, compared to Fingolimod alone, and by 6.6-fold compared to animals receiving both Fingolimod and verapamil. (That animals receiving both Fingolimod and verapamil should be less prone to 3rd-degree AV blocks is expected: verapamil slows intranodal conduction and "protects" from the effect of Fingolimod.)

In human patients, Fingolimod is counter-indicated in patients presenting a history of Mobitz Type II second-degree or third-degree AV block or sick sinus syndrome. The drug has been shown to produce AV block from the first dose, and avoiding treatment with Fingolimod and AV blockers is recommended (Fingolimod (Fingolimod) Full Prescribing Information. Novartis: T2016-22, February 2016). Given the history of translatability of the guinea pig cardiovascular data to other species, including man, these results suggest that 14:0 lyso PG could alleviate the risk of AV block associated with Fingolimod use, thus enhancing the safety profile of the drug, and allowing the treatment of patients, which cannot otherwise receive Fingolimod due to AV block issues.

Orally-administered 14:0 lyso PG has been shown to be well-tolerated in clinical trials; it is devoid of adverse effects at the exposure levels used in the curcumin Phase 1a and Phase 1b clinical trials. More importantly, it exhibited clinical efficacy against curcumin in the ongoing Phase 1b study, preventing QT and QTc interval prolongation in human patients.

In a series of experiments reproducing the reduction of the reserve of repolarization in patients taking verapamil and Fingolimod, the "regulatory standard, instrumented guinea pig" model produced preclinical results suggesting that 14:0 lyso PG can right-shift the QTc prolongation curve and limit QTc prolongation by Fingolimod in impaired patients taking other drugs, such as verapamil. At present, usage of Fingolimod by these patients is either immediately terminated or subjected to costly monitoring.

In a distinct series of experiments, Fingolimod-induced AV block was reproduced in the same instrumented guinea pig model. Administering lipids prior to Fingolimod intravenous infusion right-shifted the PR-interval vs. Fingolimod dose-response curve, moving the exposure threshold for 3rd-degree AV block by 13 fold compared to Fingolimod alone. As is the current procedure for QTc-prolonging drugs, those patients presenting a history of acquired AV block need exhaustive monitoring if receiving Fingolimod to prevent the complications associated with complete heart block.

Finally, co-administration or co-formulation of Fingolimod with 14:0 lyso PG represents a unique opportunity to prolong patent protection while improving the safety profile of this successful drug.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Chartrand, E. Arnold, A. A., Gravel, A., Jenna, G., Marcotte, I. Potential role of the membrane in hERG channel functioning and drug-induced QT prolongation. Biochim. et Biophys. Acta. 2010; 1798: 1651-1662.

Chayanupatkul M., Liangpunsakul S. Cirrhotic cardiomyopathy: review of pathophysiology and treatment. Hepatol Int. 2014 July; 8(3): 308-315.

Gilenya (Fingolimod) Full Prescribing Information. Novartis: T2016-22, February 2016.

Mitchell, L. B. Atrioventricular Block. The Merck Manual—Professional Version 2015. Merck & Co., Inc., Kenilworth, N.J., USA.

WHO Model List of Essential Medicines" (PDF). World Health Organization. October 2013.

Roden D M. Taking the idio out of idiosyncratic: predicting torsades de pointes. Pacing Clin. Electrophysiol. 1998; 21:1029-1034.

Yagi Y. et al. Analysis of Onset Mechanisms of a Sphingosine 1-Phosphate Receptor Modulator Fingolimod-Induced Atrioventricular Conduction Block and QT-Interval Prolongation. Toxicology and Applied Pharmacology. 2014: 281; 39-47.

Zeltser D, Justo D, Halkin A, et al. Drug-induced atrioventricular block: prognosis after discontinuation of the culprit drug. J Am Coll Cardiol. 2004; 44(1):105-108.

What is claimed is:

1. A method of treating a drug-induced atrioventricular (AV) block consisting of:
    identifying a subject in need of a drug therapy, wherein the drug therapy is contraindicated because it causes a drug-induced atrioventricular (AV) block and the drug therapy consists of a therapeutically effective amount of fingolimod and verapamil that causes AV block; and
    providing the subject with the therapeutically effective amount of fingolimod and verapamil, with a single dose of 1 mg/kg of 14:0 lysophosphatidylglycerol sufficient to reduce or eliminate the AV block for at least 1 to 8 hours, wherein the AV block is a third-degree AV block; and
    reducing or eliminating the drug-induced AV block by 90, 95, or 100%, wherein the lipid and drug combination are co-administered orally, enterally, parenterally, intravenously, or intraperitoneally.

2. The method of claim 1, wherein the amount of fingolimod and verapamil individually cause limited or no AV block, but when provided in combination cause a third-degree AV block.

3. A method of treating a drug-induced atrioventricular (AV) block consisting of:
    identifying a subject in need for a therapeutic treatment with a drug, wherein the drug causes AV block as a side effect and the drug is contraindicated for that subject, wherein AV block is caused by therapeutically effective amount of fingolimod and verapamil that causes AV block; and
    providing the subject with the therapeutically effective amount of fingolimod and verapamil and a single dose of 14:0 lysophosphatidylglycerol sufficient to eliminate the drug-induced AV block, wherein the AV block is a third-degree AV block; and reducing the AV block by 85, 90, 95, or 100% for at least 1 to 8 hours, wherein the lipid and drug combination are co-administered orally, enterally, parenterally, intravenously, or intraperitoneally.

4. The method of claim 3, wherein the drug is defined further as a combination of two drugs, wherein each of the drugs individually causes limited or no AV block, but when provided in combination causes an AV block.

5. A method of treating a drug-induced atrioventricular (AV) block consisting of:

identifying a subject with Mobitz Type II second-degree, third-degree AV block or sick sinus syndrome, wherein providing the subject with fingolimod is contraindicated; and prior to providing the fingolimod, providing a single dose comprising 14:0 lysophosphatidylglycerol sufficient to reduce or eliminate the AV block before providing the subject with the fingolimod, wherein the AV block is a third-degree AV block that is reduced or eliminated caused by the drug; and reducing the AV block by 95 or 100% for at least 1 to 8 hours, wherein the lipid and drug combination are administered orally, enterally, parenterally, intravenously, or intraperitoneally.

\* \* \* \* \*